United States Patent [19]

Blackburn et al.

[11] Patent Number: 4,770,998
[45] Date of Patent: Sep. 13, 1988

[54] BIOCHEMICAL ASSAY OF ALDEHYDES

[75] Inventors: Gary R. Blackburn, Washington Crossing; John F. Dooley, Newton, both of Pa.; Carl R. Mackerer, Pennington, N.J.; Ceinwen A. Schreiner, Newtown, Pa.

[73] Assignee: Mobil Oil Corporation, New York, N.Y.

[21] Appl. No.: 754,041

[22] Filed: Jul. 11, 1985

[51] Int. Cl.$^4$ ............................................. C12Q 1/32
[52] U.S. Cl. ...................... 435/26; 435/32; 435/29; 435/6
[58] Field of Search ............ 435/26, 32, 29, 240, 435/241, 6, 948

[56] References Cited

PUBLICATIONS

Casanova et al. (1984) Biochemical Pharmocology vol. 33, No. 7, pp. 1137–1142.
Steinman et al. (1968) The Journal of Biological Chemistry vol. 243, No. 4, Feb. 25 pp. 730–734.
Casanova et al. (1984) Chemical Abstracts vol. 10, No. 7, p. 163, item #49674r.
Ohono et al. (1985) Chemical Abstracts vol. 102, No. 19, p. 176, item #161692s.
Phillips et al. (1976) Chemical Abstracts vol. 85, No. 5 p. 8, item #28448f.
Torronen et al. (1981) Chemical Abstracts vol 95, No. 13, p. 193 item #109919u.
Patel et al. (1978) Chemical Abstracts vol. 90 (1979) No. 11, p. 120, item #81642u.
Clive et al. (1979) Mutation Research vol. 59, pp. 61–108.

*Primary Examiner*—Sam Rosen
*Attorney, Agent, or Firm*—Alexander J. McKillop; Michael G. Gilman; Charles J. Speciale

[57] ABSTRACT

This invention provides a biochemical method for determining the presence of toxic or mutagenic aldehyde in a test article. A sample of the test article is treated with an aldehyde dehydrogenase, such as formaldehyde dehydrogenase, and the change of growth characteristics of an indicator cell produced by the treatment are used for the determination.

9 Claims, 2 Drawing Sheets

FIG. 1 EFFECT OF FDH ON THE TOXICITY OF FORMALIN (NONACTIVATED)
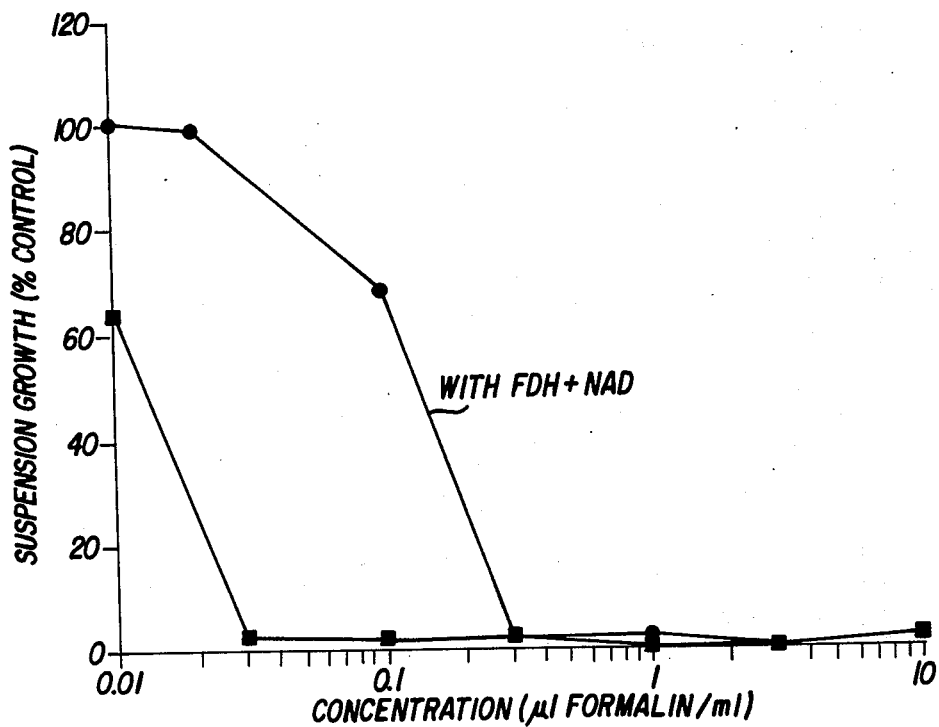
FIG. 2 EFFECT OF FDH ON THE TOXICITY OF FORMALIN (S-9 ACTIVATED)
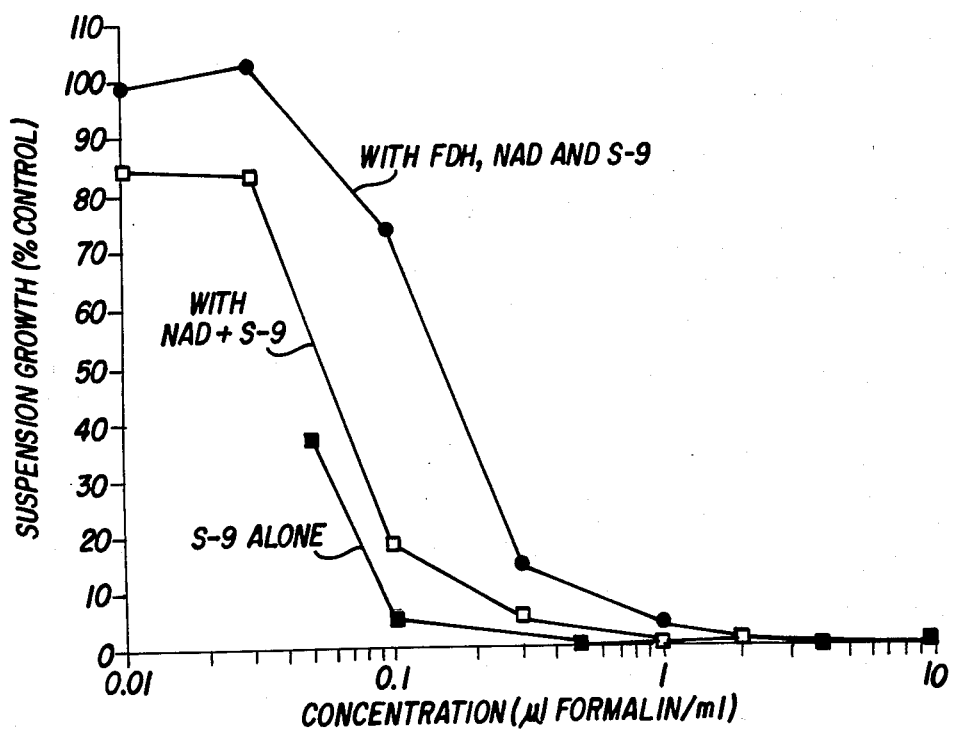

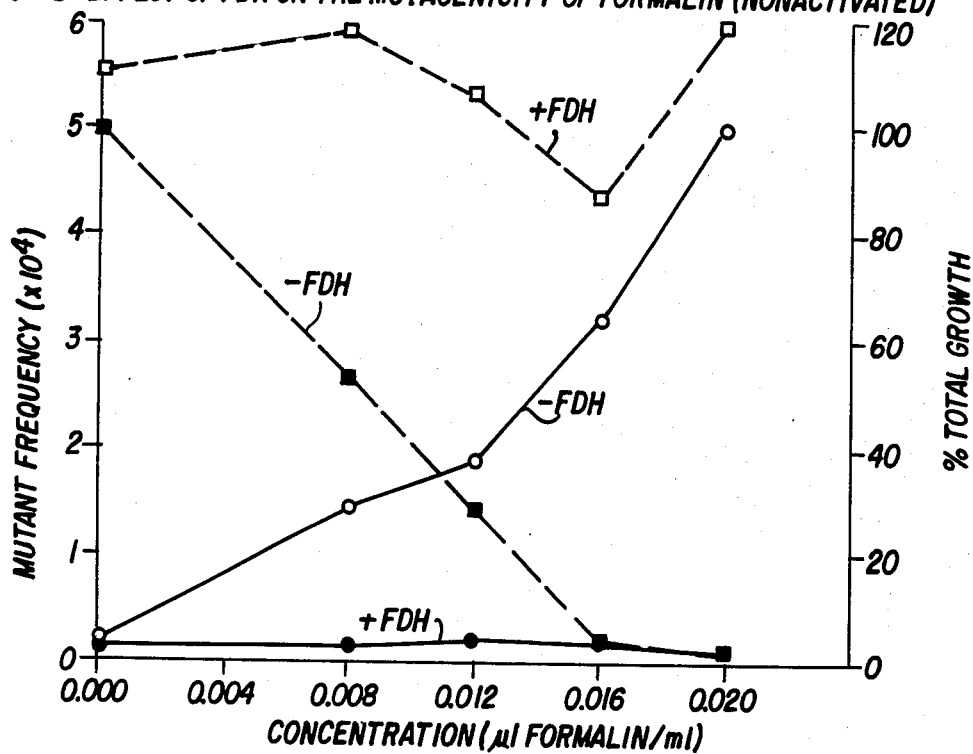
FIG. 3 EFFECT OF FDH ON THE MUTAGENICITY OF FORMALIN (NONACTIVATED)
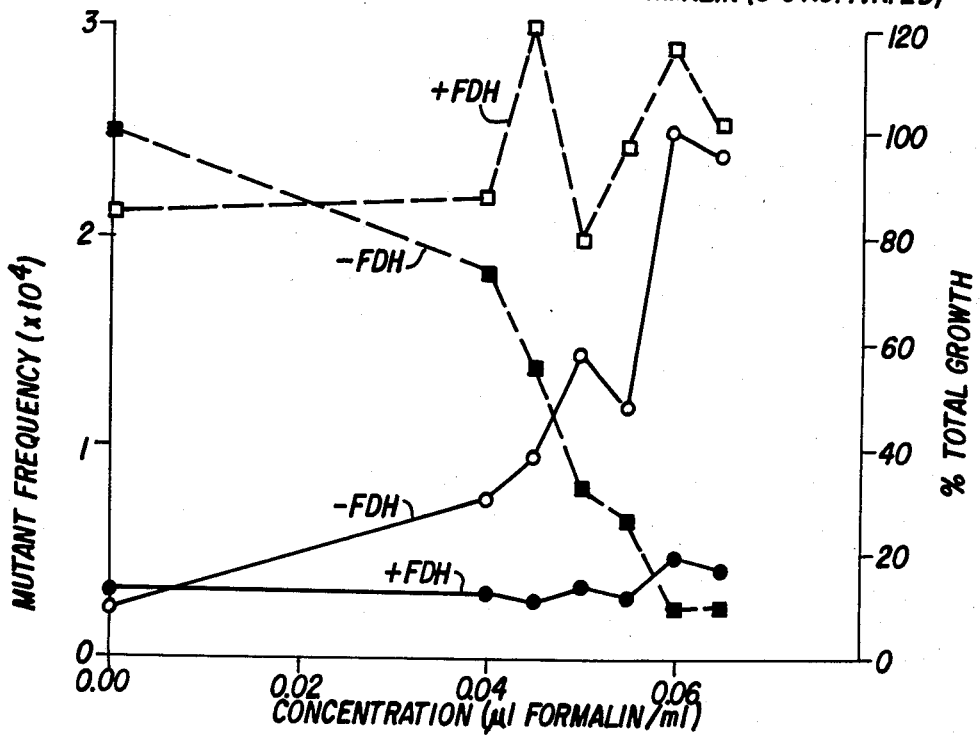
FIG. 4 EFFECT OF FDH ON THE MUTAGENICITY OF FORMALIN (S-9 ACTIVATED)

BIOCHEMICAL ASSAY OF ALDEHYDES

FIELD OF THE INVENTION

This invention is broadly concerned with the biochemical assay of mutagenic compounds in complex mixtures. It is more particularly concerned with compounds which are active substrates for enzymes, and in which either the compound itself or its enzymatically produced derivative (but not both) has pronounced toxicity and/or mutagenic activity. It is still more specifically concerned with determining, in a mixture, the presence of aldehydes, including formaldehyde.

BACKGROUND OF THE INVENTION

The aliphatic and aromatic aldehydes are known to be very reactive. In addition to being fairly readily oxidized to the corresponding acids and reduced to the alcohols, the aldehydes enter into a number of condensation reactions, such as with amines, with alcohols, and with the same or with different aldehyde compounds. These reactions need not be described here in detail since they are well known. See, for example, ENCYLOPEDIA OF CHEMICAL TECHNOLOGY, Third Edition, Volume 1, pp. 97–112 (acetaldehyde); pp. 112–123 (acetal resins); pp. 790–798 (aldehydes); and Volume 11, pp. 231–249 (formaldehyde); John Wiley & Sons, New York. The contents of these sections are incorporated herein by reference as background material.

A number of the simpler aldehyde condensation reactions are known to be reversible under appropriate conditions. A familiar example is that of aqueous formaldehyde stabilized with methanol, commonly known as formalin, in which the formaldehyde exists as an equilibrium mixture of methylene glycol, its oligomers and hemiacetals. Another example is paraldehyde $(CH_3CHO)_3$, the cyclic trimer of acetaldehyde. This condensation product, unlike acetaldehyde, does not resinify when treated with sodium hydroxide and it does not reduce silver nitrate. However, on distilling with dilute sulfuric acid, or even on heating with water, it reverts to acetaldehyde.

Formaldehyde is the most important industrially used aldehyde. Major applications include the manufacture of phenolic resins, urea resins, acetal resins, adhesives for plywood, leather, carpet, and the manufacture of protective and decorative coatings. Also of note are formaldehyde-derived biocides such as are used in metalworking oils, coatings, fuel oil, and formaldehyde-derived pharmaceuticals.

Although it has been reported that all aldehydes are toxic, with the lower, more volatile members being considered dangerous, it was only about five years ago that the mutagenic potential of formaldehyde was recognized. See, for example, "Report of the Federal Panel on Formaldehyde", ENVIRONMENTAL HEALTH PERSPECTIVES, Vol. 42, pp. 139–168, 1982, the contents of which are incorporated herein by reference for background. Recent studies have also shown formaldehyde to be carcinogenic. Very recent reports suggest that some of the other lower aldehydes also may be mutagenic.

Recognition that formaldehyde in the environment warrants more consideration than accorded a mere nuisance, and the knowledge that many formaldehyde-derived substances, per se innocuous, may in processing or in use give rise to available formaldehyde, has led to need for a method of determining the presence of low levels of available aldehyde in a wide variety of products. Conventional analytical methods are not suitable for determining low aldehyde levels in complex mixtures which may contain interfering substances. These methods are particularly not suitable for determining whether or not all of the mutagenicity of a test article already found to be mutagenic can be ascribed to a known mutagen, e.g. formaldehyde.

It is an object of this invention to provide a biochemical method for determining the presence of available aldehyde in a test article. It is a further object to determine the presence of available formaldehyde in a test article, and to estimate its concentration. It is a still further object to provide a method for determining the presence of available aldehyde in a complex mixture that contains substances which interfere with the conventional methods for determining aldehydes. These and other objects will become apparent to one skilled in the art on reading this entire specification and the appended claims.

The term "test article" as used herein means any object or substance to be tested.

The term "available" as applied herein to aldehydes means aldehyde in free, monomeric form or in some other loosely combined form (such as formalin) which has the toxic and mutagenic properties characteristic of the free aldehyde.

The term "toxic" as used herein means the property of retarding, or completely stopping, cell growth in a culture of indicator cells.

The term "mutagenic" as used herein means the ability to induce a measureable increase in the frequency of mutation of indicator cells.

The term "assay" as used herein means mutagenicity assay.

The term "indicator cell" as used herein means a bacterial or animal cell or cell line useful for detecting mutagenicity, i.e. a cell having a defined genetic locus responsive to mutagens.

BRIEF SUMMARY OF THE INVENTION

This invention provides a method for determining the presence of toxic or mutagenic aldehyde in a mutagenic test article.

In its broad aspect, the method of this invention requires that a sample of the test article be incubated with a suitable indicator cell, in the absence of, and in the presence of, a wide spectrum aldehyde dehydrogenase, under conditions which effect enzymatic conversion of the available aldehyde to the corresponding carboxylic acid, as more fully described hereinbelow. The enzyme-containing sample and the untreated sample are then compared for change in toxicity to the indicator cell, any observed reduction being relatable to metabolized aldehyde. The use of formaldehyde dehydrogenase (FDH) instead of a wide spectrum aldehyde dehydrogenase provides a determination which is specific for available formaldehyde.

For aldehydes such as formaldehyde that are mutagenic as well as toxic, one can determine the presence of available aldehyde in a test article by measuring the enzymatic reduction of mutagenicity instead of the reduction in cytotoxicity. For a first determination, toxicity is the preferred method since this requires a relatively short time to complete compared with an assay of mutagenicity. Supplementing the toxicity determination with a mutagenicity assay provides confirmation, and also indicates whether or not the available mutagenic aldehyde is the sole mutagen in the test article, as further illustrated by the examples given below.

BRIEF DESCRIPTION OF THE DRAWING

FIG. 1: Effect of FDH on cytotoxicity of formalin.
FIG. 2: Effect of S-9 on cytotoxicity of formalin.
FIG. 3: Mutagenic Assay of Formalin, Lymphoma cells, without S-9 activation.
FIG. 4: Mutagenic Assay of Formalin, Lymphoma cells, with S-9 activation.

DETAILED DESCRIPTION AND SPECIFIC EMBODIMENTS

This invention may be used to determine the presence of any aldehyde, preferably any aldehyde having up to seven carbon atoms, that can be transformed by an enzyme with marked reduction of toxicity, or of mutagenicity, or of both. The method of this invention requires the use of an indicator cell that has a growth pattern which, in the absence of a test article, is unaffected by supplementation with an aldehyde dehydrogenase and cofactor. However, the method of this invention is not restricted to the use of any particular indicator cell provided it meets the requirement just recited.

In the interest of clarity, it is believed that this invention is now best described by providing descriptions of:

(1) a preferred indicator cell;
(2) a method for storage, maintenance and cultivation of the preferred indicator cell (protocol) which provides accurate assays by the method of this invention;
(3) Control Articles and Test Articles
(4) Example 1, showing that the control growth rate of the preferred indicator cell is unaffected by the enzyme system (formaldehyde dehydrogenase), but that the growth rate is dose responsive to formalin, and that both enzyme and nicotinamide adenine dinucleotide (NAD) cofactor are required to suppress the toxicity of formalin.
(5) Example 2, illustrating the effect of S-9 liver homogenate on toxicity of formalin;
(6) Example 3, illustrating nonactivated mutagenicity assay of formalin; and
(7) Example 4, illustrating activated mutagenicity assay of formalin.

All of the foregoing examples and the others included in this specification are given for illustrative purposes only, and are not to be construed as limiting the scope of this invention, which scope is determined by this entire specification including the appended claims.

A Preferred Indicator Cell

Mouse lymphoma L5178Y cells (clone 3.7.2C) ATCC CRL 9518 are preferred since these indicator cells are useful for mutagenicity as well as for toxicity assay. This genetic variant is heterozygous at the Thymidine kinase (TK) locus (TK+/−) and it may undergo a single-step forward mutation to the TK-deficient homozygote (TK−/−), in which little or no TK activity remains. This mutant is viable in normal medium because its DNA synthesis proceeds by a de novo synthetic pathway (thymidylate synthetase) that does not involve thymidine as an intermediate. It is also viable in trifluorothimidine (TFT)-containing medium because of its inability to phosphorylate TFT to a lethal mononucleotide. Thus, TFT can be used to select for TK-deficient cells and against TK-competent cells. Cells which grow to form colonies in the presence of TFT are assumed to have mutated, either spontaneously or by the action of the test article, to the TK−/−phenotype.

Protocol for Preferred Indicator Cell

The procedures used are essentially those described for the mouse lymphoma mutagenisis assay by Dr. Clive et al. in Mutation Research, 59, 61–108 (1979), the entire content of which is incorporated herein by reference.

The L5178Y mouse lymphoma indicator cells (clone 3.7.2C) are stored in liquid nitrogen. Cultures are thawed and are maintained in logarithmic growth by serial subculturing for up to six weeks. Cultures are grown at 37° C. in either a shaker incubator or a roller-harvester incubator. A cell-stock log is kept to record cell densities and subculture procedures. Cultures are cleansed on a weekly basis, as described by Clive et al. (1979), to reduce the frequency of spontaneous TK−/− mutants and thus maintain minimum mutant frequencies in the negative controls.

The medium for suspension culture of the cells is Fischer's medium (for leukemic mice) supplemented with heat-inactivated horse serum (10%, v/v), sodium pyruvate (1 mM) and Pluronic (0.1%, w/v). This medium is further supplemented with gentamycin (20 ug/ml) and Noble agar (0.34%, w/v) for cloning cultures in semi-solid agar. The selection medium is cloning medium supplemented with TFT (2.5 ug/ml).

Control Articles

If the test article is dosed neat or as a solution in water, the negative control cultures are left untreated. Should a solvent be used for the test article, the negative control article is the solvent. The final concentration of solvent in such case is no more than 1% (100 ul/10 ml media). The negative control cultures for test articles assayed with S-9 activation includes the solvent and the activation mixture.

The positive control article for nonactivated assay is ethylmethane sulfonate (EMS) which is highly mutagenic via alkylation of cellular DNA. It is used at 0.5 and 1.0 ul/ml. The positive control article for S-9 activated assays is 7,12-dimethylbenz[a]anthracene (DMBA) which requires metabolic activation by microsomal enzymes to become mutagenic. It is used at 2.5 and 5.0 ug/ml.

Test Articles

If the test article is a water soluble solid, it is dissolved in a solvent, preferably water. If the test article is not soluble in water at concentrations of 10 mg/ml (solids) or 0.1 ml/ml (liquids), its solubility is determined at these concentrations in DMSO, ethanol, acetone, methanol, acetonitrile, EGDE and THF. If complete solubility is not achieved in one of these solvents, the solvent giving the highest solubility will be used. Sonication and heating (to 37° C.) may be used to aid in the solubilization or dispersion of the test articles.

Initial Toxicity Determination

After the selection of a suitable solvent, an initial toxicity determination is conducted to establish an appropriate concentration range for evaluating the mutagenicity of the test article. This determination is performed with and without S-9 activation unless contraindicated. Organic solvent-soluble test articles are tested for cytotoxicity at either 1000, 500, 100, 50, 10 and 5 ug/ml (solids) or 1.0, 0.5, 0.1, 0.05, 0.01 and 0.005 ul/ml (liquids); water soluble test articles are tested over similar ranges but at 10-fold higher concentrations. After an exposure time of 3 hours at 37° C., the cells are resuspended in growth medium and incubated for 24 hours, using procedures identical to those for the mutagenesis assay. Cell population densities are determined after 24 hours to measure growth rates of test article-treated cultures relative to solvent-treated cultures. Cultures may be readjusted to $6 \times 10^6$ cells in 20 mls growth medium per tube and incubated for an additional 24 hours to further quantitate test article-induced cytotoxicity. Ten to 14 doses for mutagenicity testing will then be interpolated between the concentration producing approximately 90% cytotoxicity (10% relative suspension growth) and that producing approximately 10% cyctotoxicity (90% relative suspension growth).

Mutagenicity Assay

The nonactivated and S-9 activated assays of the test article may be performed concurrently; however, they are independent assays with their own positive and negative controls. The procedures used for these assays are based on methods described by Clive et al. (1979), and are identical except for the addition of the S-9 mix during the 3-hour treatment period in the S-9 activated assay. The S-9 mix consists of the S-9 fraction of rat liver homogenate (0.25 ml S-9 ml) and required cofactors, nicotinamide adenine dinucleotide phosphate (8 mg/ml) and isocitric acid (15 mg/ml). The S-9 homogenate is obtained commercially (Microbiological Associates) and consists of a $9000 \times g$ supernatant prepared from Aroclor 1254-induced adult male rat livers.

Logarithmically growing cultures of recently cleansed lymphoma cells are counted and adjusted to $1 \times 10^6$ cells/ml for use in the assays. Six mls of this cell suspension are seeded into a series of culture tubes (1 tube per treatment, unless contraindicated). The tubes are labeled with the name and concentration of the test article, positive control or negative control and with NA or S-9 for nonactivated and S-9 activated assays, respectively. Four mls of growth medium (without serum) or four mls of S-9 mix is then added to the tubes, depending upon whether they receive S-9 activation. In the FDH/NAD supplemented cultures, the NAD is added in the FOP or the S-9 mix to give a final concentration of 8.1 mM. The FDH, at a final concentration of 0.09 Units/ml, is added just prior to dosing in 250 μls of FOP. The dosed tubes are incubated at 37° C. for 3 hours in a roller drum. Following exposure, the cells are washed twice, resuspended in 20 mls growth medium and reincubated.

An expression period of 2 days is used to allow recovery, growth and expression of the TK−/− phenotype. Cell population densities will be determined on Day 1 (approximately 24 hours after treatment) and is adjusted to $3 \times 10^5$ cells/ml to maintain optimal growth rates. Cell population densities are then determined on Day 2 (approximately 44 hours after treatment), and appropriated cultures selected for mutant analysis. Four to 8 concentrations will normally be selected for analysis, with emphasis on moderately toxic (approximately 50% relative suspension growth) to highly toxic (approximately 5–10% relative suspension growth) treatments. Cultures with cell densities less than $1.5 \times 10^5$ cells/ml will not be considered for analysis.

Each culture selected for analysis is evaluated for mutation induction and cloning efficiency. For analysis of mutation induction, $3 \times 10^6$ cells from each culture will be suspended in selection medium and evenly distributed into three 100 mm petri dishes (labeled TFT) so that each dish contains approximately $1 \times 10^6$ cells. For analysis of cloning efficiency, each culture is serially diluted and seeded into three 100 mm petri dishes (labeled VC) so that each dish contains approximately 200 cells in cloning medium. All dishes are placed in 37° C. incubator with 5% carbon dioxide and 95% humidified air for colony development. After 10 to 12 days incubation, the colonies are counted with an electronic colony counter (Biotran III). All tests preferably are performed in duplicate.

The mutant frequency is calculated by dividing the average number of mutant colonies per dish (from the three mutant selection dishes) by the average number of viable colonies per dish (from the three cloning efficiency dishes) and multiplying by $2 \times 10^4$.

The percent total growth for each culture is calculated by multiplying its relative suspension growth over the 2-day expression period by its relative cloning efficiency and dividing by 100%. This value provides a measure of the toxicity of each treatment and is used to evaluate cell and test article interaction and as a basis for selecting doses for any repeat trials that may be necessary.

In a preferred embodiment of this invention, available formaldehyde is assayed using formaldehyde dehydrogenase (FDH) plus cofactor nicotinamide adenine dinucleotide (NAD). The use of mouse lymphoma cultures as indicator cells permits assay by elimination of toxicity, which is rapid, but also confirmation by elimination of mutagenicity, which is more time consuming. This preferred embodiment will now be described in detail. The FDH, derived from *Pseudomomas putida*, Enzyme Commission designation EC 1.2.1.1 was purchased from Sigma Chemical Company, St. Louis, Mo., as was the NAD. The mouse lymphoma culture was originally obtained from Burroughs Welcome, Research Triangle Park, N.C.

Examples

EXAMPLE 1

In this example, lymphoma cultures were exposed to formalin over a range of concentrations from 0.1 to 10 ul/ml with and without formaldehyde dehydrogenase (FDH) plus nicotinamide adenine dinucleotide (NAD) in the absence of metabolic activation. Formalin contains 37% formaldehyde, therefore, 1 ul formalin/ml is equivalent to 0.37 mg formaldehyde/ml. After 3 hours, the exposure medium was removed and the cultures were washed, refed and reincubated. After 24 hours, the cultures were counted and the relative suspension growths were calculated.

Shown in FIG. 1, formalin was completely toxic at concentrations above 0.03 ul/ml. In contrast, a 10-fold higher concentration of formalin was necessary to produce similar levels of toxicity, that is reduction in suspension growth, in the presence of FDH and NAD. The suspension growth curves for cultures treated with formalin and FDH alone, or with formalin and NAD alone, were super-imposable on the control curve. Thus, the reduction in the toxicity of formaldehyde is dependent upon the combined presence of FDH and NAD in nonactivated cultures.

EXAMPLE 2

Example 1 was repeated to assess the effect of rat liver homogenate (S-9) activation on toxicity. S-9 alone, NAD plus S-9, and FDH with NAD and S-9 were run. The results on toxicity are shown in FIG. 2.

The addition of FDH and NAD reduced the toxicity of formalin in the presence of S-9 activation. However, in contrast to nonactivated cultures, the addition of NAD to S-9 activated cultures provided a small measure of protection from the toxicity of formalin. This suggests that FDH or other NAD-dependent nonspecific dehydrogenases are present in the S-9 mix.

EXAMPLE 3

In this example the dose-dependent mutagenic effect of formaldehyde on lymphoma cultures, both with and without FDH plus NAD, was investigated in the absence of S-9 activation. The results are shown in FIG. 3, where mutant frequency is expressed as mutants per $10^4$ surviving cells and is indicated by the solid lines. Total growth is a measure of toxicity which combines relative suspension growth and relative cloning growth (or efficiency); it is expressed as a percent of the nontreated control culture and is indicated by the broken lines.

As shown in FIG. 3, formalin produced a significant dose-dependent increase in mutant frequency and a dose-dependent reduction in total growth. In contrast, formalin was not toxic or mutagenic at these same concentrations in cultures supplemented with FDH and NAD.

EXAMPLE 4

Example 3 was repeated but with S-9 activation. The results are shown in FIG. 4. As with Example 3, the presence of FDH plus NAD eliminated both the mutagenicity and the toxicity of formalin.

Examples 5 and 6 show that FDH plus NAD are ineffective for reducing either the toxicity or the mutagenicity of the positive test articles. Neither EMS nor DMBA would be expected to give rise to available formaldehyde.

EXAMPLE 5

Example 3 was repeated, substituting ethylmethane sulfonate (EMS) at the 0.5 and 1.0 ul/ml levels for formalin. EMS is known to be highly mutagenic via alkylating cellular DNA.

No reduction of toxicity or mutagenicity was found with addition of FDH plus NAD.

EXAMPLE 6

Example 4 was repeated, substituting 7,12-dimethylbenz[a]anthracene (DMBA) at the 2.5 and 5.0 ug/ml level for formalin. DMBA is known to require metabolic activation by microsomal enzymes to become mutagenic.

No reduction of toxicity or mutagencity was found with addition of FDH plus NAD.

EXAMPLE 7

Tris-(hydroxymethyl) nitromethane (TNM) is a biocide, used commonly in cutting oils, that has been known to stoichiometrically release formaldehyde, 3 mols of formaldehyde per mol of TNM. Example 3 was repeated, substituting TNM for the formalin. Dose dependent increases in toxicity and mutagenicity were found in the absence of FDH plus NAD, and absent in its presence. An estimate of the available formaldehyde based on the dose producing 50% toxicity indicated that all of the combined formaldehyde was available.

Example 8 illustrates the method of this invention to determine if the mutagenicity of a complex coating formulation was attributable to formaldehyde.

EXAMPLE 8

An emulsion resin coating intended for use as a can-liner for spray cans was initially found to be significantly mutagenic in the five-strain tests performed according to the method of Ames et al., *Mut. Res.* 31, 347–364 (1975), which publication is incorporated herein by reference. This method employs strains of *Salmonella typhimurium*. Mutagenicity was confirmed in the mouse lymphoma assay described herein. Addition of FDH eliminated mutagenicity, implicating formaldehyde as the principal, if not the sole mutagen.

It was known that the resin incorporated in the coating mixture did contain a small amount of formaldehyde, but this amount was very inadequate to account for the observed level of mutagenicity. Accordingly, measures were taken, such as fractionating the coating and examining the fractions, as well as assaying components of the coating, for an explanation.

As a result of the study, it was found that a cross-linking agent commercially known under the trade name "Cymel", which was incorporated in the coating during manufacture, gave rise to most of the mutagenicity found for the coating. The cross-linking agent was an amine-formaldehyde condensation product, which decomposed to provide the significant mutagenic levels of formaldehyde found in the final coating.

EQUIVALENTS

Although this invention has been described above with reference to the particular embodiment which utilizes mouse lymphoma as indicator cells, and FDH as the enzyme, it will be recognized by those skilled in the art that other indicator cells and other aldehyde dehydrogenases also may be used. For example, it is contemplated to use the cell line CHO (Chinese hamster ovary) instead of the mouse lymphoma cell. This cell is on deposit with American Type Culture Collection under the designation ATCC CCL 61 CHO-K1. It is also contemplated, e.g., to use yeast aldehyde dehydrogenase, Enzyme Commission designation E.C. 1.2.1.5. The properties of the homogeneous aldehyde preparation are given by Steinman et al. in *Jour. Biological Chem.*, 243, No. 4, February 25, pp. 730–734 (1968), the contents of which are incorporated herein by reference. As can be seen from that publication, this dehydrogenase is characterizable as a wide-spectrum type.

It is also contemplated to use the indicator-cell method of this invention to determine the presence of compounds other than aldehydes, which compounds either are mutagenic per se, or are capable of enzymatic transformation to mutagens.

What is claimed is:

1. A biochemical method for determining the presence of toxic or mutagenic aldehyde in a test article, which method comprises:
   (a) selecting a biological indicator cell with a well-characterized genetic locus for the detection of mutagens, and that has a growth rate substantially unaffected by supplementation with aldehyde dehydrogenase and cofactor;

(b) exposing said indicator cell to a sample of said test article in the presence of an added aldehyde dehydrogenase and cofactor under conditions effective to enzymatically convert said aldehyde to non-toxic or non-mutagenic product;

(c) incubating said exposed cell whereby determining its growth characteristics;

(d) duplicating steps (b) and (c) in the absence of added aldehyde dehydrogenase and cofactor; and, (e) determining the presence of said aldehyde from the change in growth characteristics induced by said added aldehyde dehydrogenase and cofactor.

2. The method of claim 1 wherein the available toxic aldehyde of said test article is determined.

3. The method of claim 1 wherein the available mutagenic aldehyde is determined.

4. The method of claim 1 wherein said selected indicator cell is L5178Y mouse lymphoma cells (clone 3.7.2C), ATCC CRL 9518.

5. The method of claim 4 wherein said aldehyde dehydrogenase is yeast and wherein the content of available toxicaldehyde of said test article is estimated.

6. The method of claim 4 wherein said aldehyde dehydrogenase is formaldehyde dehydrogenase and wherein the content of available formaldehyde in the test article is estimated.

7. The method of claim 1 wherein said selected indicator cell is Chinese hamster ovary (CHO), ATCC CCL 61 CHO-K1.

8. The method of claim 7 wherein said aldehyde dehydrogenase is yeast dehydrogenase.

9. The method of claim 7 wherein said aldehyde dehydrogenase is formaldehyde dehydrogenase.

* * * * *